United States Patent [19]

Tohzuka et al.

[11] 4,284,822
[45] Aug. 18, 1981

[54] PROCESS FOR PREPARING HEXAFLUOROACETONE

[75] Inventors: Takashi Tohzuka, Settsu; Yohnosuke Ohsaka, Takatsuki, both of Japan

[73] Assignee: Daikin Kogyo Co., Ltd., Osaka, Japan

[21] Appl. No.: 135,164

[22] Filed: Mar. 28, 1980

[30] Foreign Application Priority Data

Mar. 31, 1979 [JP] Japan .................................. 54-38694

[51] Int. Cl.³ ............................................. C07C 45/32
[52] U.S. Cl. .............................. 568/399; 260/544 F; 570/17 S
[58] Field of Search ................................ 568/399, 400

[56] References Cited

U.S. PATENT DOCUMENTS

| | | | |
|---|---|---|---|
| 3,636,156 | 1/1972 | Ozaki et al. | 568/400 |
| 3,925,481 | 12/1972 | Geus | 568/400 |
| 4,057,584 | 11/1972 | Tohzuka et al. | 568/400 |
| 4,165,340 | 8/1979 | Tohzuka et al. | 568/399 |

*Primary Examiner*—Howard T. Mars
*Assistant Examiner*—James H. Reamer
*Attorney, Agent, or Firm*—Birch, Stewart, Kolasch & Birch

[57] ABSTRACT

Hexafluoroacetone is prepared by reacting hexafluoropropene with oxygen in the presence of a metal oxide selected from the group consisting of tin oxides, iron oxides and indium oxides. These metal oxides can be readily handled and assure a stable reaction.

3 Claims, No Drawings

PROCESS FOR PREPARING HEXAFLUOROACETONE

This invention relates to a process for preparing hexafluoroacetone. More particularly, it relates to a process for preparing hexafluoroacetone from hexafluoropropene in the presence of a certain specific catalyst.

Hexafluoroacetone is useful as a catalyst for polymerization of perfluorocyclobutene or triazine. Further, fluoroacetone itself is polymerizable and is used as a monomeric component for ethylene/hexafluoroacetone/tetrafluoroethylene terpolymer. Furthermore, hexafluoroacetone is used as a raw material of bisphenol AF (($C_6H_4OH)_2C(CF_3)_2$), which is a cross-linking agent for fluoroelastomers.

For preparation of hexafluoroacetone, there are known some processes including a process comprising reacting hexafluoropropene with oxygen in the presence of fluorinated alumina or fluorinated silica alumina as a catalyst (cf. U.S. Pat. No. 4,057,584 and Japanese Patent Publication (unexamined) No. 25513/1978). The said catalysts are, however, too sensitive to handle the reaction reasily. When the conversion of the starting monomer is increased, sometimes a runaway state takes place.

In order to overcome such defects, an extensive study has been made, and as the result, it has been found that certain metal oxides are highly effective catalysts in the reaction between hexafluoropropene and oxygen. The present invention is based on this finding.

According to the present invention, there is provided a process for preparing hexafluoroacetone which comprises reacting hexafluoropropene with oxygen in the presence of a metal oxide selected from the group consisting of tin oxides, iron oxides and indium oxides.

The said metal oxide can be easily handled, and the reaction in the presence of such metal oxide can be carried out smoothly and stably even when the conversion of hexafluoropropene is high. The metal oxide is any commercially available one. Prior to the use as the catalyst, it is preferably dried or heated in an atmosphere of an inert gas such as nitrogen at a temperature of from 200° to 700° C., preferably from 300° to 500° C. Among tin oxides, tin(IV) oxide is preferred. Oxides of tin of lower atomic valency may be also effective since they can be converted into tin(IV) oxide during the reaction. Among iron oxides, iron(III) oxide is favorable. However, oxides of iron of lower atomic valency may also be effective for the same reason as in the case of tin oxides. As indium oxides, indium(III) oxide is favorably used.

After use over a long period of time, carbon is deposited on the surface of the metal oxide particle so that the catalytic activity is much lowered. In such case, the deteriorated catalyst can be reactivated by heating it in an oxygen or oxygen-containing atmosphere such as air at a temperature of from 350° to 500° C.

The process of the invention is carried out by contacting a mixture of hexafluoropropene and oxygen with the metal oxide in a per se conventional manner. For example, the mixture is contacted batchwise or continuously with a fixed bed, a moving bed or a fluidized bed containing the catalyst in a suitable reactor.

The molar ratio of hexafluoropropene and oxygen is usually from 1:10 to 1:0.1, particularly from 1:2 to 1:0.3. When the proportion of oxygen is lower than the said lower limit, only a lower conversion of hexafluoropropene is achieved. When the proportion of oxygen is higher than the said upper limit, the yield of hexafluoroacetone tends to decrease. When desired, the mixture may be diluted with an inert gas such as carbon dioxide, nitrogen or helium.

The reaction temperature is usually from 150° to 300° C., preferably from 200° to 270° C. At a lower temperature, the conversion of hexafluoropropene is decreased, and at a higher temperature, the yield of hexafluoroacetone is lowered. Thus, hexafluoropropene is hardly reacted at a temperature lower than 150° C., and hexafluoroacetone is produced in a very low yield at a temperature higher than 300° C.

Any particular limitation is not present on the reaction pressure, and atmospheric or higher pressure is usually employed. In general, a higher pressure is preferred to obtain a higher conversion and a better yield. At an industrial scale, a pressure of from 0 to 20 $Kg/cm^2G$ is normally employed.

The contact time may depend on other reaction conditions, particularly with the reaction temperature. At a higher temperature, the contact time is shorter, and at a lower temperature, it is longer. In general, it may be from 0.5 second to 30 minutes. When the contact time is longer, the conversion of hexafluoropropene increases. Thus, a suitable contact time should be selected from the viewpoint of production efficiency. For example, when the contact is effected continuously at a temperature of from about 200° to 270° C., the preferred contact time is selected from 1 second to 10 minutes.

The present invention will be hereinafter explained in detail by the following Examples.

EXAMPLE 1

Tin(IV) oxide (20–50 mesh) was heated in a nitrogen stream at 350° C. for 3 hours. The tin oxide (5 g) was charged into a glass tube of 3 mm in inner diameter and 0.5 m in length. A mixture of oxygen and hexafluoropropene in a molar ratio of 1:2 was fed into the glass tube at 220° C. or 250° C. under atmospheric pressure with a contact time of 40 seconds. The exit gas was analyzed by gas chromatography. The results, the conversion of hexafluoropropene and the selectivity of hexafluoroacetone, are shown in Table 1.

TABLE 1

| Temp. (°C.) | Exit gas compositon (mole %) | | | | | Conversion (%) | Selectivity (%) |
| --- | --- | --- | --- | --- | --- | --- | --- |
| | $CF_4$ | $COF_2$ | $C_3F_6$ | $(CF_3)_2CO$ | High b.p. materials | | |
| 220 | 23.4 | 12.7 | 46.2 | 17.0 | 0.3 | 39.1 | 57.2 |
| 250 | 36.0 | 21.0 | 18.2 | 23.6 | 1.2 | 70.6 | 53.9 |

EXAMPLE 2

Tin(IV) oxide was shaped into pellets of 5 mm in diameter and 3 mm in length and heated in a nitrogen stream at 350° C. for 5 hours. The pellets (30 g) were charged into a Hastelloy C made tubular reactor of 0.5 inch in diameter. The reactor was sustained in a molten salt bath kept at 220° C. Then, a mixture of oxygen and hexafluoropropene in a molar ratio of 1:2 was fed into the reactor under atmospheric pressure with a space velocity of 80 $hr^{-1}$. The exit gas was analyzed by gas chromatography. The results, the conversion of hexafluoropropene and the selectivity of hexafluoroacetone, are shown in Table 2.

TABLE 2

| Exit gas composition (mole %) | | | | | Conversion (%) | Selectivity (%) |
|---|---|---|---|---|---|---|
| CF$_4$ | COF$_2$ | C$_3$F$_6$ | (CF$_3$)$_2$CO | High b.p. materials | | |
| 27.3 | 15.4 | 35.8 | 20.5 | 1.0 | 49.9 | 57.4 |

EXAMPLE 3

Iron(III) oxide (20-50 mesh) was heated as in Example 1. The iron oxide (4.3 g) was charged into a glass tube of 3 mm in diameter and 0.5 m in length. A mixture of oxygen and hexafluoropropene in a molar ratio of 1:2 was fed into the reactor under the same conditions as in Example 1. The exit gas was analyzed by gas chromatography. The results, the conversion of hexafluoropropene and the selectivity of hexafluoroacetone, are shown in Table 3.

TABLE 3

| Temp. (°C.) | Exit gas composition (mole %) | | | | | Conversion (%) | Selectivity (%) |
|---|---|---|---|---|---|---|---|
| | COF$_2$ | CF$_3$COF | C$_3$F$_6$ | (CF$_3$)$_2$CO | High b.p. materials | | |
| 220 | 9.2 | 5.7 | 74.9 | 9.1 | 1.1 | 18.7 | 53.3 |
| 250 | 24.2 | 13.5 | 40.2 | 20.5 | 1.6 | 49.3 | 52.4 |

EXAMPLE 4

In the same manner as in Example 2 but substituting Fe$_2$O$_3$ for SnO$_2$, the reaction was carried out. The results are shown in Table 4.

TABLE 4

| Exit gas composition (mole %) | | | | | Conversion (%) | Selectivity (%) |
|---|---|---|---|---|---|---|
| COF$_2$ | CF$_3$COF | C$_3$F$_6$ | (CF$_3$)$_2$CO | High b.p. materials | | |
| 13.2 | 7.5 | 65.7 | 12.3 | 1.3 | 25.9 | 53.5 |

EXAMPLE 5

Indium(III) oxide (20-50 mesh) was heated in nitrogen stream at 350° C. for 5 hours. The indium oxide (2.8 g) was charged into a glass tube of 3 mm in diameter and 0.5 m in length. A mixture of oxygen and hexafluoropropene in a molar ratio of 1:2 was fed into the reactor under atmospheric pressure at 250° C. with a contact time of 40 seconds. The exit gas was analyzed as in Example 1 to obtain the results as shown in Table 5.

TABLE 5

| Exit gas composition (mole %) | | | | | Conversion (%) | Selectivity (%) |
|---|---|---|---|---|---|---|
| COF$_2$ | CF$_3$COF | C$_3$F$_6$ | (CF$_3$)$_2$CO | High b.p. materials | | |
| 26.8 | 15.0 | 35.4 | 21.8 | 1.0 | 54.1 | 52.2 |

COMPARATIVE EXAMPLE

In the same manner as in Example 1 but substituting V$_2$O$_5$, PbO$_2$ or PdO for SnO$_2$ and adopting only 250° C. as the reaction temperature, the reaction was carried out. The results are shown in Table 6.

TABLE 6

| Metal | Exit gas composition (mole %) | | | | | |
|---|---|---|---|---|---|---|
| | CF$_4$ | COF$_2$ | CF$_3$COF | C$_3$F$_6$ | (CF$_3$)$_2$CO | High b.p. materials |
| V$_2$O$_5$ | 0.0 | 28.8 | 22.5 | 31.0 | 6.3 | 4.7 |
| PbO$_2$ | 0.0 | 31.2 | 23.1 | 38.0 | 4.0 | 3.7 |
| PdO | 4.0 | 34.5 | 48.7 | 4.1 | 7.5 | 1.2 |

What is claimed is:

1. A process for preparing hexafluoroacetone which comprises reacting hexafluoropropene with oxygen in the presence of a metal oxide selected from the group consisting of tin oxides, iron oxides and indium oxides.

2. The process according to claim 1, wherein the reaction temperature is from 150° to 300° C.

3. The process according to claim 1 or claim 2, wherein the molar ratio of hexafluoropropene and oxygen is from 1:0.1 to 1:10.

* * * * *